(12) United States Patent
Deng

(10) Patent No.: US 9,290,471 B2
(45) Date of Patent: Mar. 22, 2016

(54) DISPERSANT, DISPERSION OF COLOR PIGMENT, AND PHOTOSENSITIVE RESIST

(71) Applicant: BOE TECHNOLOGY GROUP CO., LTD., Beijing (CN)

(72) Inventor: Wei Deng, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 14/351,912

(22) PCT Filed: Nov. 15, 2013

(86) PCT No.: PCT/CN2013/087258
§ 371 (c)(1),
(2) Date: Apr. 15, 2014

(87) PCT Pub. No.: WO2014/176890
PCT Pub. Date: Nov. 6, 2014

(65) Prior Publication Data
US 2015/0203463 A1    Jul. 23, 2015

(30) Foreign Application Priority Data

Apr. 28, 2013  (CN) .......................... 2013 1 0156027

(51) Int. Cl.
| | | |
|---|---|---|
| *G03F 7/004* | (2006.01) |
| *C07D 307/89* | (2006.01) |
| *C08K 5/1539* | (2006.01) |
| *G03F 7/027* | (2006.01) |
| *C09B 67/08* | (2006.01) |
| *C09B 67/00* | (2006.01) |
| *C08F 8/32* | (2006.01) |

(52) U.S. Cl.
CPC ............ *C07D 307/89* (2013.01); *C08K 5/1539* (2013.01); *G03F 7/004* (2013.01); *G03F 7/027* (2013.01); *C08F 8/32* (2013.01); *C09B 67/001* (2013.01); *C09B 67/0022* (2013.01)

(58) Field of Classification Search
CPC ... C09B 67/001; C09B 67/0022; G03F 7/091; C08F 8/32; C08F 220/34
USPC .......................................... 430/270.1, 285.1
See application file for complete search history.

(56) References Cited

U.S. PATENT DOCUMENTS

| | | | | |
|---|---|---|---|---|
| 6,583,197 | B1 * | 6/2003 | Wada et al. ..................... 522/84 |
| 7,582,585 | B2 * | 9/2009 | Trefonas et al. ............... 502/171 |
| 8,029,877 | B2 * | 10/2011 | Hayashi et al. ................ 428/1.1 |
| 8,053,490 | B2 * | 11/2011 | Jia et al. ........................ 523/113 |
| 2005/0181299 | A1 | 8/2005 | Trefonas, III et al. |
| 2009/0134366 | A1 * | 5/2009 | Shibatani et al. ............. 252/582 |
| 2011/0200921 | A1 * | 8/2011 | Lee et al. .......................... 430/7 |

FOREIGN PATENT DOCUMENTS

| | | |
|---|---|---|
| CN | 1670623 A | 9/2005 |
| CN | 102039100 A | 5/2011 |
| CN | 102197098 A | 9/2011 |
| CN | 103263872 A | 8/2013 |

OTHER PUBLICATIONS

English Abstract of CN 102039100 (no date).*
International Search Report mailed Feb. 27, 2014; PCT/CN2013/087258.
First Chinese Office Action dated Jun. 20, 2014; Appln. No. 201310156027.5.
Second Chinese Office Action dated Jan. 6, 2015; Appln. No. 201310156027.5.
International Preliminary Report on Patentability Appln. No. PCT/CN2013/087258; Dated Nov. 3, 2015.

* cited by examiner

*Primary Examiner* — Amanda C Walke
(74) *Attorney, Agent, or Firm* — Ladas & Parry LLP

(57) ABSTRACT

A dispersant for preparing a dispersion of color pigments, a dispersion of color pigments including the dispersant, and a photosensitive resist including the dispersion of color pigments are disclosed. The dispersant is an amine-based dispersant including a photo-crosslinkable or photo-dimerizable group containing an anhydride functional group. The dispersant improves the developing property of photosensitive resists.

13 Claims, No Drawings

DISPERSANT, DISPERSION OF COLOR PIGMENT, AND PHOTOSENSITIVE RESIST

INVENTION FIELD

The embodiments of the present invention relate to a dispersant for preparing a dispersion of color pigment, a dispersion of color pigment containing the dispersant, and a photosensitive resist containing the dispersion of color pigment.

BACKGROUND

In display apparatuses, color negative photosensitive resists are commonly used in preparation of various parts of color filters, especially, the black shading layers, color filter pixels, supporting bulges, surface protective layers, and the like. The negative photosensitive resists can also used in various processes, such as, laser etching of semi-conductor, preparation of electrodes, etc.

Color negative photosensitive resists comprise generally dispersion of refined pigments, alkali-soluble resins, polymerizable monomers or resins, photoinitiators, modifying adjuvants, solvents, and the like. In general, the dispersion of refined pigments can be prepared by refining particles having different colors and structures. The dispersion of refined pigments can be prepared by breaking the aggregates of pigment particles during inter-collision of zirconium beads and glass beads, followed by coating the surface of particles with dispersant molecules. Micromolecular dispersing aids may be sometimes added to enhance the interaction between the dispersant molecules and the surface of pigments. Further incorporation of dispersing resins into the dispersion of refined pigments can effectively reduce the re-aggregation of the refined particles and improve the stability of the dispersion system.

SUMMARY OF INVENTION

The embodiment of the present invention provides a dispersant for preparing a dispersion of color pigments, a dispersion of color pigments containing the dispersant, and a photosensitive resist containing the dispersion of color pigments.

The dispersant for preparing the dispersion of color pigments in accordance with the embodiments of the present invention can be an amine-based dispersant comprising a photo-crosslinkable or photo-dimerizable group containing anhydride functional group.

In one aspect, the amine-based dispersant can be alkanolamine or polyamine compounds.

The photo-crosslinkable or photo-dimerizable group containing anhydride functional group can be derived from 4-acryloyloxyethyl trimellitic anhydride, 4-methylacryloyloxyethyl trimellitic anhydride, 4-cinnamoyltriethylene glycol trimellitic anhydride, 4-allylether oxyethyl trimellitic anhydride, 4-acryloxyl oxybutyl trimellitic anhydride, 4-methylacryloxyl oxybutyl trimellitic anhydride or 4-(7-ethylene glycol coumarinyl) trimellitic anhydride. These groups can taka part in the polymerization or dimerization during the light exposure so as to further stabilize the crosslinked network, thereby facilitating improving the development and the dispersing stability during high-temperature post-backing process.

Another embodiment of the present invention provides a method of preparing a dispersant for preparing a dispersion of color pigments, comprising reacting an amine-based dispersant with a photo-crosslinkable or photo-dimerizable group containing an anhydride functional group to produce a dispersant for preparing a dispersion of color pigments.

In one aspect, the reaction may occur in an organic solvent in the presence of a polymerization inhibitor under stirring at a temperature of 20 to 50° C.

In another aspect, the organic solvent can be propylene glycol methyl ether acetate, ethyl 3-ethoxypropriate, butanone, or cyclohexane.

In yet another aspect, the photo-crosslinkable or photo-dimerizable group containing an anhydride functional group can be derived from 4-acryloyloxyethyl trimellitic anhydride, 4-methylacryloyloxyethyl trimellitic anhydride, 4-cinnamoyltriethylene glycol trimellitic anhydride, 4-allylether oxyethyl trimellitic anhydride, 4-acryloxyl oxybutyl trimellitic anhydride, 4-methylacryloxyl oxybutyl trimellitic anhydride or 4-(7-ethylene glycol coumarinyl) trimellitic anhydride.

In still another aspect, the amine-based dispersant can be alkanolamine or polyamine compounds.

The molar ratio of the amino functional group of the amine-based dispersant to the photo-crosslinkable or photo-dimerizable group containing an anhydride functional group can be 2:1 to 200:1.

In still another aspect, the 4-mefhylacryloyloxyethyl trimellitic anhydride can be obtained by reacting chlorinated trimellitic anhydride, hydroxyethyl methacrylate with pyridine in the presence of a solvent of toluene.

The weight ratio of the chlorinated trimellitic anhydride, the hydroxyethyl methacrylate and the pyridine can be 210:116:80 to 440:116:80.

Alternatively, the 4-cinnamoyltriethylene glycol trimellitic anhydride can be obtained by the reaction of chlorinated trimellitic anhydride, triethylene mono-cinnamate, and pyridine in the presence of a solvent of toluene.

The weight ratio of the chlorinated trimellitic anhydride, the triethylene mono-cinnamate and the pyridine can be 210:280:80 to 440:280:80.

Alternatively, the 4-methylacryloxyl oxybutyl trimellitic anhydride can be obtained by the reaction of chlorinated trimellitic anhydride, hydroxybutyl methacrylate and pyridine in the presence of a solvent of toluene.

The weight ratio of the chlorinated trimellitic anhydride, the hydroxybutyl methacrylate and the pyridine can be 210:158:80 to 440:158:80.

The dispersant for preparing the dispersion of color pigments can be stably stored under shading conditions.

Another embodiment of the present invention provides a dispersion of color pigments, wherein the dispersant as used is the aforesaid dispersant for preparing a dispersion of color pigments.

Still another embodiment of the present invention provides a color photosensitive resist comprising a dispersion of color pigments, wherein the dispersion of color pigments is the aforesaid dispersion of color pigments.

The dispersant for preparing the dispersion of color pigments in accordance with the embodiments of the present invention incorporates a photo-crosslinkable or photo-dimerizable group containing an anhydride functional group into the amine-based dispersant. During UV exposure, the photo-crosslinkable group in the dispersant takes part in the polymerization reaction and enters into the photo-crosslinked photosensitive resist system, thereby facilitating the developing property of the photosensitive resist and the thermal stability of pixels during the post-backing process at 220° C., and facilitating avoiding over-developing phenomenon and improving the developing property of the photosensitive resist.

DETAILED EMBODIMENTS OF INVENTION

The photo-crosslinkable or photo-dimerizable group containing dispersant for preparing a dispersion of color pigments in accordance with the embodiments of the present invention is an amine-based dispersant incorporating a photo-crosslinkable or photo-dimerizable group containing an anhydride functional group.

In particular, the amine-based dispersant is alkanolamine or polyamine compounds, wherein the anchored group is amino group, such as, 24000, 32500, 76500, and J200 available from Lubrizol; 6919, 160, 161, 162, 163, 167, 2000, 2001, 2152, 9150, and 9152 available from BYK; and the like.

In particular, the photo-crosslinkable or photo-dimerizable group containing an anhydride functional group can be derived from 4-acryloyloxyethyl trimellitic anhydride, 4-methylacryloyloxyethyl trimellitic anhydride, 4-cinnamoyltriethylene glycol trimellitic anhydride, 4-allylether oxyethyl trimellitic anhydride, 4-acryloxyl oxybutyl trimellitic anhydride, 4-methylacryloxyl oxybutyl trimellitic anhydride or 4-(7-ethylene glycol coumarinyl) trimellitic anhydride. All of the groups can take part in polymerization or dimerization during light exposure so as to further stabilize the crosslinked network, thereby facilitating the development and the dispersing stability during the high-temperature post-backing process.

The embodiments of the present invention introduce a photo-crosslinkable or photo-dimerizable group containing an anhydride functional group into the amine-based polymeric dispersant by the modification of the active hydrogen in the amine group of the amine-based polymeric dispersant. Under the reaction conditions, the anhydride moiety of the photo-crosslinkable or photo-dimerizable group containing an anhydride functional group can be reacted not only with the amine group, but also with other hydroxylated functional groups. The photosensitive resist prepared by using the dispersant in accordance with the present invention exhibits improved developing property and improved stability of post-baking since the photo-crosslinkable group in the dispersant takes part in the polymerization reaction and enters into the crosslinked photosensitive resist during the UV exposure process.

Another embodiment of the present invention provides a method of preparing a dispersant for preparing a dispersion of color pigments comprising reacting an amine-based dispersant with a photo-crosslinkable or photo-dimerizable group containing an anhydride functional group to prepare the dispersant for preparing the dispersion of color pigments.

In one aspect, the reaction occurs in an organic solvent in the presence of a polymerization inhibitor under stirring at a temperature of 20 to 50° C.

For instance, the organic solvent can be propylene glycol methyl ether acetate, ethyl 3-ethoxypropriate, butanone or cyclohexanone.

In another aspect, the photo-crosslinkable or photo-dimerizable group containing an anhydride functional group can be derived from 4-acryloyloxyethyl trimellitic anhydride, 4-methylacryloyloxyethyl trimellitic anhydride, 4-cinnamoyltriethylene glycol trimellitic anhydride, 4-allylether oxyethyl trimellitic anhydride, 4-acryloxyl oxybutyl trimellitic anhydride, 4-methylacryloxyl oxybutyl trimellitic anhydride or 4-(7-ethylene glycol coumarinyl) trimellitic anhydride.

In yet another aspect, the amine-based dispersant is alkanolamine or polyamine compounds, such as, 24000, 32500, 76500, and J200 available from Lubrizol; 6919, 160, 161, 162, 163, 167, 2000, 2001, 2152, 9150, 9152 available from BYK; and the like.

There is an amino group present in the amine-based dispersant, and under the reaction conditions, the anhydride moiety of the photo-crosslinkable or photo-dimerizable group containing an anhydride functional group can be reacted not only with the amino group, but also with other hydroxylated functional groups. Through these reactions, a photo-crosslinkable or photo-dimerizable group is introduced into the amine-based dispersant molecule.

In yet another aspect, the molar ratio of the amine-based dispersant to the photo-crosslinkable or photo-dimerizable group containing an anhydride functional group can be 2:1 to 200:1.

In yet another aspect, 4-methylacryloyloxyethyl trimellitic anhydride can be obtained by the reaction of chlorinated trimellitic anhydride, hydroxyethyl methacrylate and pyridine in the presence of a solvent of toluene.

Among others, the weight ratio of chlorinated trimellitic anhydride, the hydroxyethyl methacrylate and the pyridine can be 210:116:80 to 440:116:8.

Alternatively, 4-cinnamoyltriethylene glycol trimellitic anhydride can be obtained by the reaction of chlorinated trimellitic anhydride, triethylene mono-cinnamate and pyridine in the presence of a solvent of toluene.

The weight ratio of the chlorinated trimellitic anhydride, the triethylene mono-cinnamate and the pyridine can be 210:280:80 to 440:280:80.

Alternatively, 4-methylacryloxyl oxybutyl trimellitic anhydride can be obtained by the reaction of chlorinated trimellitic anhydride, hydroxybutyl methacrylate and pyridine in the presence of a solvent of toluene.

Among others, the weight ratio of chlorinated trimellitic anhydride, the hydroxybutyl methacrylate and the pyridine can be 210:158:80 to 440:158:80.

EXAMPLES

Preparation Example 1

210 parts by weight of small particles of chlorinated trimellitic anhydride and 2000 parts by weight of toluene were fed into a three-neck flask provided with a thermometer, a stirrer, and a drop funnel. Then, 116 parts by weight of hydroxyethyl methacrylate, 80 parts by weight of pyridine, and 2000 parts by weight of toluene were added dropwise with the drop funnel. The reaction temperature was controlled below 5° C. by using an ice-water bath. After completion of addition, the reaction mixture was stirred at room temperature f 4 hours, stood, and filtered. 0.1 parts by weight of p-t-butyl-catechol were added into the filtrate as the polymerization inhibitor. The solvent of toluene was removed by evaporation under reduced pressure to give 4-methylacryloyloxyethyl trimellitic anhydride.

288 parts by weight of 4-methylacryloyloxyethyl trimellitic anhydride solids were added to 3000 parts by weight of an amine-based dispersant (Lubrizol 24000) and 6000 parts by weight of propylene glycol methyl ether acetate, and then 0.2 parts by weight of a polymerization inhibitor were added. The reaction mixture was stirred for 12 hours at a temperature controlled as 50° C., to give the dispersant for preparing the dispersion of color pigments.

Preparation Example 2

210 parts by weight of small particles of chlorinated trimellitic anhydride and 2000 parts by weight of toluene were fed into a three-neck flask provided a thermometer, a stirrer, and a drop funnel. Then, 156 parts by weight of hydroxybutyl methacrylate, 80 parts by weight of pyridine, and 2000 parts by weight of toluene were added dropwise with the drop funnel, and the temperature was controlled below 5° C. by using an ice-water bath. After completion of addition, the reaction mixture was stirred at room temperature, stood, and filtered. 0.1 parts by weight of p-t-butyl-catechol were added into the filtrate as a polymerization inhibitor. The solvent of toluene was removed by evaporation under reduced pressure to give 4-methylacryloxyl oxybutyl trimellitic anhydride.

329 parts by weight of 4-methylacryloxyl oxybutyl trimellitic anhydride were added to 3000 parts by weight of amine-based dispersant (Lubrizol 24000) and 6000 parts by weight of propylene glycol methyl ether acetate, and then 0.2 parts by weight of polymerization inhibitor were added. The reaction mixture was stirred for 12 hours and the temperature was controlled as room temperature, to give a dispersant for preparing a dispersion of color pigments.

Preparation Examples 3

210 parts by weight of small particles of chlorinated trimellitic anhydride and 2000 parts by weight of toluene were fed to a three-neck flask provided with a thermometer, a stirrer, and a drop funnel. Then, 280 parts by weight of triethylene monocinnamate, 80 parts by weight of pyridine and 2000 parts by weight of toluene were added dropwise, and the temperature was controlled below 5° C. by using an ice-water bath. After completion of addition, the reaction mixture was stirred at room temperature for 4 hours, stood, and filtered. The solvent of toluene was removed by evaporation under reduced pressure, to give 4-cinnamoyltriethylene glycol trimellitic anhydride.

453 parts by weight of 4-cinnamoyltriethylene glycol trimellitic anhydride were added to 3000 parts by weight of amine-based dispersant (Lubrizol 24000) and 6000 parts by weight of propylene glycol methyl ether acetate, and then 0.2 parts by weight of polymerization inhibitor were added. The reaction mixture was stirred for 12 hours and the temperature was controlled as room temperature, to give a dispersant for preparing a dispersion of color pigments.

Application Examples

Dispersions of color pigments were prepared with the dispersants prepared in accordance with the aforesaid Preparation Examples 1 to 3 and the commercially available Lubrizol 24000 as follows:

a): 80 g of dispersant, 40 g of dispersing resin 2388, and 350 g of solvent PMA were mixed and stirred for 1 hour;

b): 100 g of red pigment PR254 was added to the dispersion prepared in step a), the mixture was stirred for 1 hour;

c): 500 g of solvent PMA was added into the dispersion prepared in step b), and the mixture was grinded and dispersed for 2 hours, to give the dispersion of pigments.

Color photosensitive resists were prepared with the above-prepared dispersions of color pigments as follows: 200 g of the above-prepared dispersion of color pigments, 75 g of alkali-soluble resin SB401, 25 g of photosensitive resin DPHA, 6 g of photoinitiator 379 6 g, 8 g of adjuvant 361N, 4 g of adjuvant 432, and 450 g of solvent PMA were mixed and stirred for 5 hours, to give the color photosensitive resist.

In accordance with the aforesaid procedures, color filters were prepared by using the above-prepared color photosensitive resists as follows:

Step 1): coating a glass substrate with the above-prepared color photosensitive resist;

Step 2): the glass substrate obtained in step 1) was pre-baked at a temperature of 150° C. for 2 minutes, and then exposed to UV radiation with an exposure energy of 150 mJ/cm; and Step 3): the glass substrate undergoing step 2) was developed in an alkali developer, and then baked at a temperature of 250° C. for 30 minutes, to give the color filters.

The properties of the obtained color filters are shown in Table 1.

TABLE 1

| | Application Example 1 | Application Example 2 | Application Example 3 | Comparative Application Example 1 |
|---|---|---|---|---|
| Dispersant | Preparation Example 1 | Preparation Example 2 | Preparation Example 3 | Lubrizol 24000 |
| Resolution of Developing property | ++ | ++ | ++ | + |
| Time Margin of Development | ++ | ++ | + | + |
| Stability of Post-Baking | ++ | ++ | + | + |

Among others, "+" represents average level, and "++" represents superior.

It can be seen from the above results that as compared with the photosensitive resist prepared by using the currently available dispersants, the photosensitive resists prepared by using the dispersants in accordance with the embodiments of the present invention exhibits a higher resolution, a higher time margin of development, and an improved stability of post-baking because the photo-crosslinkable group in the dispersant takes part in the polymerization and enters into the crosslinked photosensitive resist during UV exposure process.

Finally, it is understood that the aforesaid examples are only for the purpose of illustrating the technical solutions of the present invention, other than limiting the scope thereof. Although the present invention is illustrated in details with reference to the aforesaid embodiments, a person of ordinary skill in the art should understand that the technical solutions of the above embodiments can still be modified, or some technical features thereof can be equivalently substituted. Such modifications or substitutions will not result in that the nature of corresponding technical solutions depart from the spirit and scope of various embodiments of the present invention.

I claim:

1. A dispersant, which is an amine-based dispersant comprising a group selected from an anhydride functional group-containing photo-crosslinkable group and an anhydride functional group-containing photo-dimerizable group,
   wherein the amine-based dispersant is selected from alkanolamine and polyamine compounds,
   wherein the group selected from an anhydride functional group-containing photo-crosslinkable group and an anhydride functional group-containing photo-dimerizable group is derived from a group selected from 4-acryloyloxyethyl trimellitic anhydride, 4-methylacryloyloxyethyl trimellitic anhydride, 4-cinnamoyltriethylene glycol trimellitic anhydride, 4-allylether oxyethyl trimellitic anhydride, 4-acryloxyl oxybutyl trimellitic anhydride, 4-methylacryloxyl oxybutyl trimellitic anhydride and 4-(7-ethylene glycol coumarinyl) trimellitic anhydride.

2. A method of preparing a dispersant for preparing a dispersion of color pigments, said method comprising:
reacting an amine-based dispersant with a group selected from an anhydride functional group-containing photo-crosslinkable group and an anhydride functional group-containing photo-dimerizable group to prepare the dispersant for preparing the dispersion of color pigments,
wherein the amine-based dispersant is selected from alkanolamine and polyamine compounds,
wherein the group selected from an anhydride functional group-containing photo-crosslinkable group and an anhydride functional group-containing photo-dimerizable group is derived from a group selected from 4-acryloyloxyethyl trimellitic anhydride, 4-methylacryloyloxyethyl trimellitic anhydride, 4-cinnamoyltriethylene glycol trimellitic anhydride, 4-allylether oxyethyl trimellitic anhydride, 4-acryloxyl oxybutyl trimellitic anhydride, 4-methylacryloxyl oxybutyl trimellitic anhydride and 4-(7-ethylene glycol coumarinyl) trimellitic anhydride.

3. The method of claim 2, wherein the reaction occurs in an organic solvent in the presence of a polymer inhibitor under stirring at a temperature of 20 to 50° C.

4. The method of claim 3, wherein the organic solvent is selected from the group consisting of propylene glycol methyl ether acetate, ethyl 3-ethoxypropriate, butanone and cyclohexanone.

5. The method of claim 2, wherein the molar ratio of the amino functional group of the amine-based dispersant to the group selected from an anhydride functional group-containing photo-crosslinkable group and an anhydride functional group-containing photo-dimerizable group is 2:1 to 200:1.

6. The method of claim 2, wherein the 4-methylacryloxyethyl trimellitic anhydride is prepared by the reaction of chlorinated trimellitic anhydride, hydroxyethyl methacrylate and pyridine in the presence of a solvent of toluene.

7. The method of claim 6, wherein the weight ratio of chlorinated trimellitic anhydride, hydroxyethyl acrylate and pyridine is 210:116:80 to 440:116:80.

8. The method of claim 2, wherein the 4-cinnamoyltriethylene glycol trimellitic anhydride is prepared by the reaction of chlorinated trimellitic anhydride, triethylene mono-cinnamate and pyridine in the presence of a solvent of toluene.

9. The method of claim 8, wherein the weight ratio of chlorinated trimellitic anhydride, triethylene mono-cinnamate and pyridine is 210:280:80 to 440:280:80.

10. The method of claim 2, wherein the 4-methylacryloxyl oxybutyl trimellitic anhydride is prepared by the reaction of chlorinated trimellitic anhydride, hydroxybutyl methacrylate and pyridine in the presence of a solvent of toluene.

11. The method of claim 10, wherein the weight ratio of chlorinated trimellitic anhydride, hydroxybutyl methacrylate and pyridine is 210:158:80 to 440:158:80.

12. A dispersion of color pigments, wherein the dispersant used in the dispersion of color pigments is the dispersant for preparing the dispersion of color pigments in accordance with claim 1.

13. A color photosensitive resist comprising a dispersion of color pigments, wherein the dispersion of color pigments is the dispersion of color pigments in accordance with claim 12.

* * * * *